Figure 1:
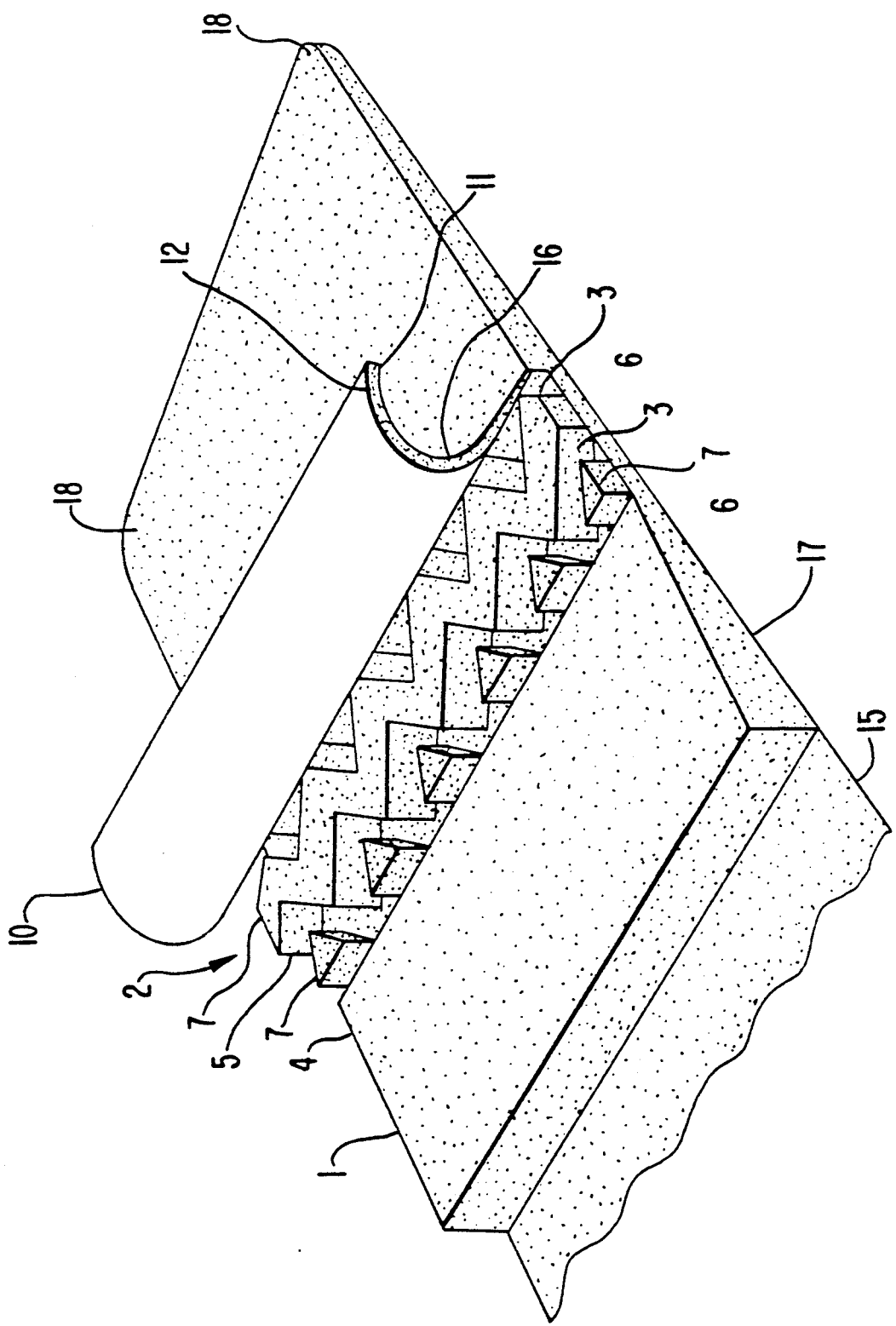

United States Patent [19]

Gerhartl

[11] Patent Number: 5,125,401

[45] Date of Patent: Jun. 30, 1992

[54] COMPRESS FOR DRESSING WOUNDS

[75] Inventor: Gerd Gerhartl, Bichwil, Switzerland

[73] Assignee: Flawa Schweizer Verbandstoff- und Wattefabriken AG, Flawil, Switzerland

[21] Appl. No.: 514,024

[22] Filed: Apr. 27, 1990

[30] Foreign Application Priority Data

Apr. 27, 1989 [CH] Switzerland .......... 1607/89

[51] Int. Cl.⁵ .......... A61F 13/00; A61F 15/00; A61L 15/00
[52] U.S. Cl. .......... 602/45; 604/380; 602/52; 602/58
[58] Field of Search .......... 128/155, 156, 82.1; 604/380

[56] References Cited

U.S. PATENT DOCUMENTS

| 1,863,333 | 6/1932 | Heitmeyer | 604/380 |
| 2,822,509 | 2/1958 | Harvey | 128/156 |
| 2,896,618 | 7/1959 | Schaefer | 128/155 |
| 3,967,623 | 7/1976 | Butterworth et al. | 128/156 |
| 3,993,820 | 11/1976 | Repke | 604/380 |
| 4,381,784 | 5/1983 | Aberson et al. | 128/156 |
| 4,619,252 | 10/1986 | Ibbott | 128/82.1 |
| 4,624,666 | 11/1986 | De Rossett et al. | 604/380 |
| 4,817,594 | 4/1989 | Juhasz | 128/155 |
| 4,930,500 | 6/1990 | Morgan | 128/155 |

Primary Examiner—Randall L. Green
Assistant Examiner—Paul Prebilic
Attorney, Agent, or Firm—Wegner, Cantor, Mueller & Player

[57] ABSTRACT

A compress for dressing wounds contains a depot layer (1) for storing liquids. A guiding layer (2) is assigned to the side of the depot layer (1) which faces the front side of the compress, which guiding layer is constructed in such a manner that the secretion which reaches it can spread out predominantly along said layer (2), before it reaches the depot layer (1). In order to achieve this effect, channels (3) are formed in the surface of the guiding layer (2) which faces the front side of the compress. Said channels (3) extend in the direction of the surface of the guiding layer (2). The two layers (1, 2) are arranged between a surface ply (10) and a lower sealing layer (15), the edges (16, 17) of which are bonded. Liquids which reach the surface layer spread out rapidly and evenly over the entire surface of the compress.

22 Claims, 3 Drawing Sheets

COMPRESS FOR DRESSING WOUNDS

The present invention relates to a compress for dressing wounds, having a pad for storing the secretion from the wound.

Known compresses of this type have a pad which is made of an absorbent material, for example cottonwool. Said pad is situated in a thin sheath, which is intended in particular to prevent individual fibers becoming detached from the cottonwool pad. Compresses of this type function in a manner such that the wound secretion is sucked away from the wound and the secretion is then stored in the material of the pad.

Compresses are generally constructed as a two-dimensional structure. Normally, the surface of the compress is larger than the surface of the wound. The compress is placed on the wound as far as possible so that the wound is located beneath the central region of the compress. As a result, the secretion coming from the wound goes to the central region of the compress. If the region of the compress lying on the wound is saturated with the wound secretion, the secretion then builds up between the compress and the wound. This happens because the secretion in the direction of the surface of the pad material can only seep through slowly into said material. If the wound secretion which builds up between the wound and the compress dries, a scab is then formed therefrom, one side of which adheres to the wound and the other side of which to the compress. If the compress is removed, the wound will be reopened, which has known and undesirable consequences.

It is also known to make the sheath material, at least on the side of the pad facing the wound, from a material which is especially smooth and less likely to adhere to the wound. However, this measure does not help if a large amount of secretion leaves the wound and if a scab is formed, because the relevant area of the sheath material is included in the scab and, when the compress is removed, the wound is likewise reopened.

The object of the present invention is to provide a compress which does not have the mentioned or any other disadvantages.

This object is achieved by the compress of the type mentioned at the outset according to the invention, as defined in the characterizing clause of claim 1.

Figure 2:
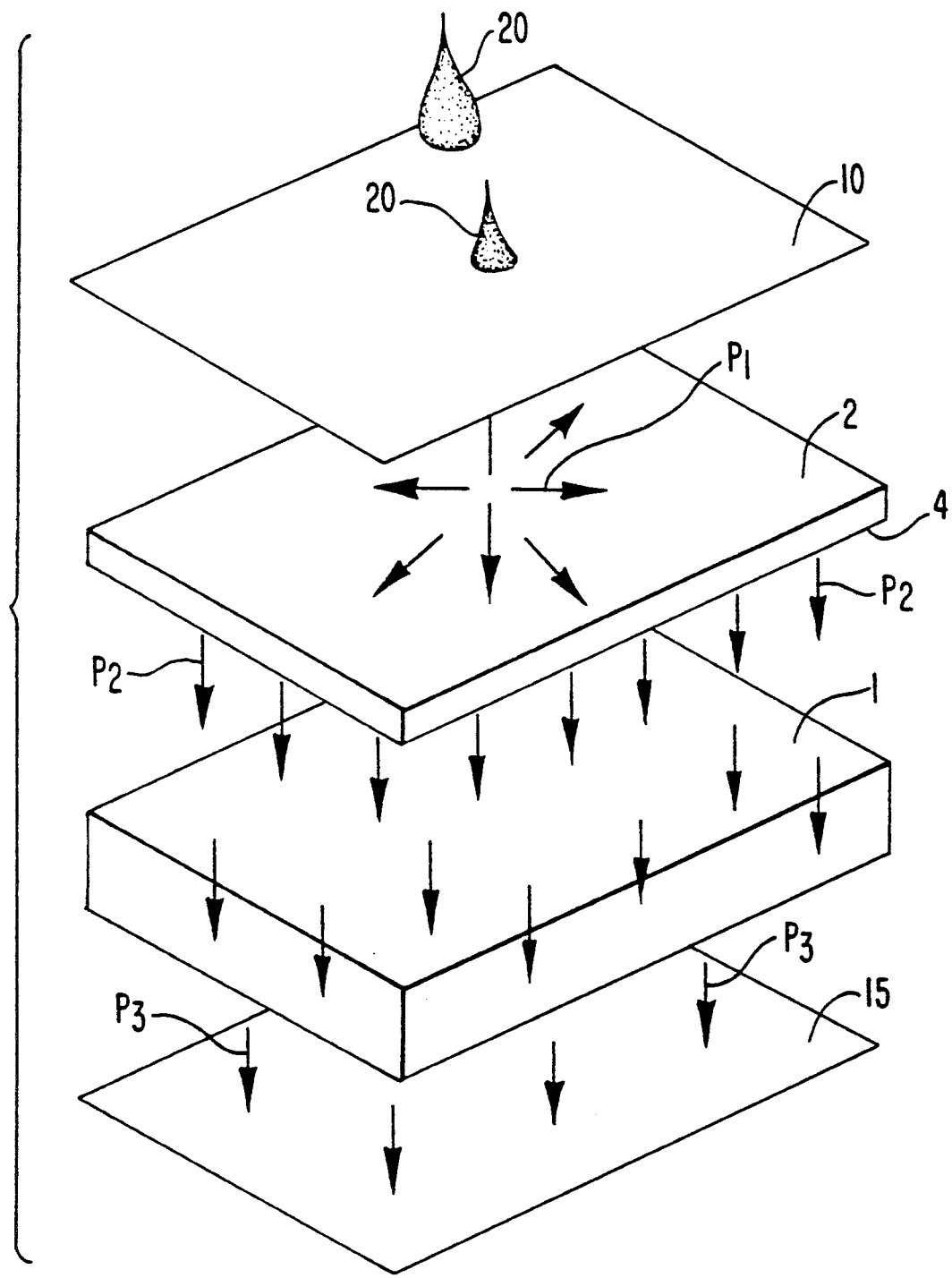
Figure 3:
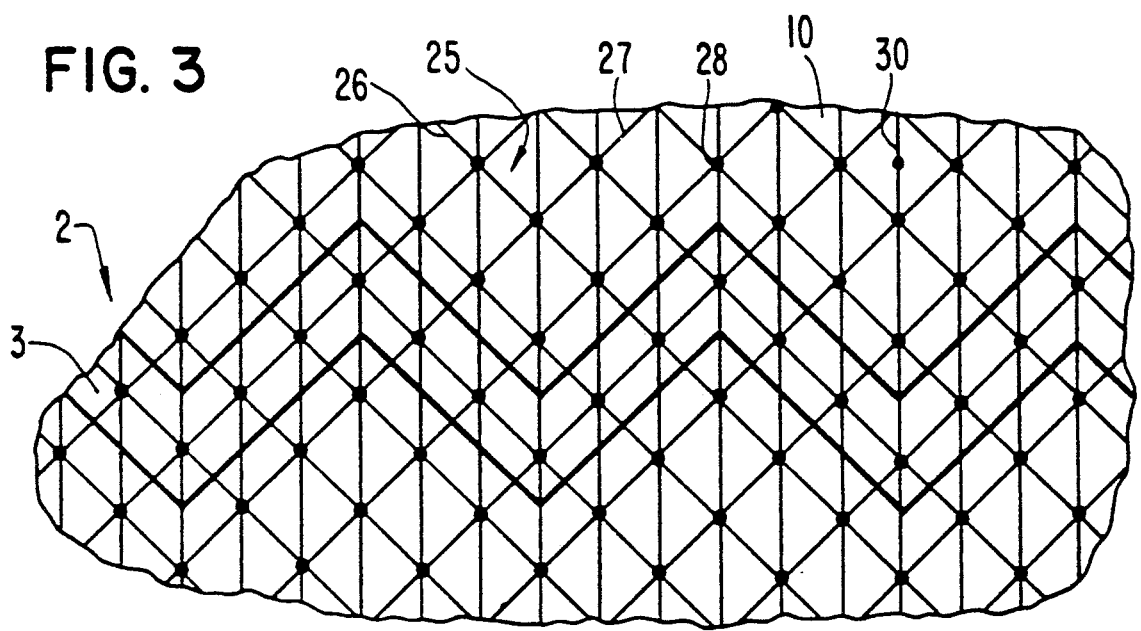
Figure 4:
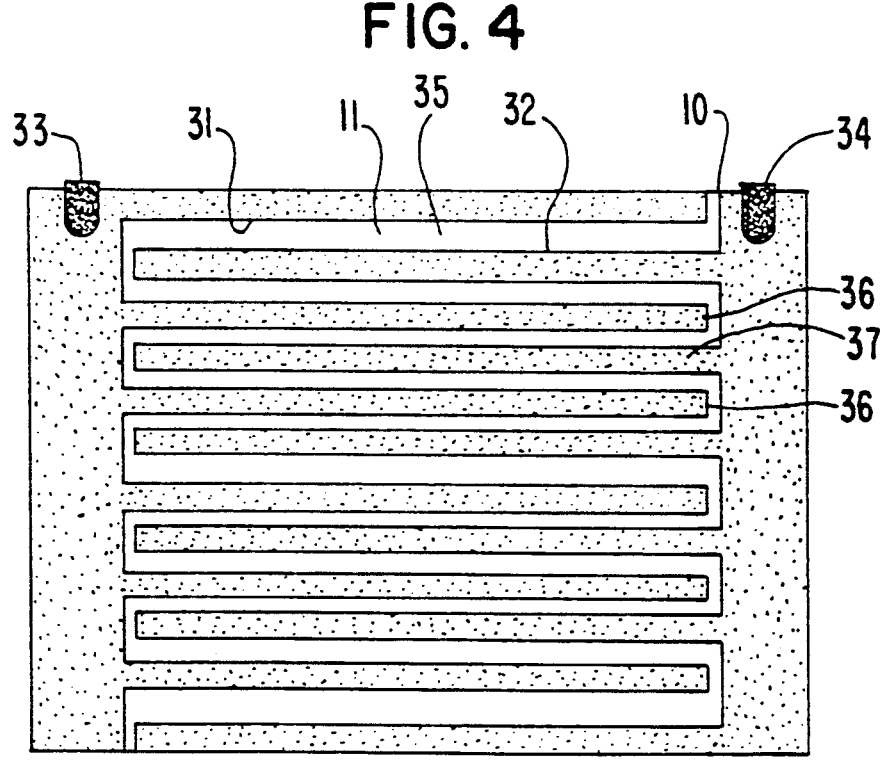

Embodiments of the present invention are illustrated in more detail below with reference to the attached drawings, in which:

FIG. 1 shows in perspective and partially in the rolled up state the present compress, FIG. 2 shows schematically in an exploded view the compress according to FIG. 1, this illustration intending to illustrate the function of the present compress, FIG. 3 shows a plan view of a section of a further embodiment of the present compress, in which the surface of the compress is provided with a netting-type spacer and FIG. 4 shows a plan view of another embodiment of the present compress, in which the surface of the compress is provided with electrodes.

The present compress (FIG. 1) for dressing wounds has a thin and two-dimensional structure, which may, for example, be square. The compress may be approximately 3 mm thick and the size and shape thereof may be adapted to the particular use. The compress has superposed layers 1, 2, 10 and 15, which are connected one under another, so that the compress forms a whole. The corners 18 of the compress are rounded.

The lowermost layer 15 of the compress is drawn in elongated form in the front region of FIG. 1 so as to illustrate said layer 15 more clearly, although in the finished product it also ends near to the edge of layer 1 lying thereupon. Said last mentioned layer 1 consists of loosely carded cottonwool, which is indicated by the wedge-shaped profile of the exposed section of said layer 1 which can be seen from this drawing. The left section of the uppermost ply 10 is partly rolled up, so that the layers 1 and 2 therebelow can be seen. The layer 2 located between the uppermost ply 10 and the layer of cottonwool 1 is shown in shortened form relative to the layer of cottonwool 1, so that a section of the layer of cottonwool 1 can also be seen from above.

The side of the compress which is to be in contact with a wound will be referred to here as the front or wound side of the compress. The present invention is based on the knowledge that, in order for the wound secretion to be distributed quickly over the surface of the compress, it is of vital importance how the compress is layered and how the thicknesses in the individual layers are located and distributed.

The thickest layer of the present compress constitutes a so-called depot layer 1, which serves to store the secretion coming from a wound. Moreover, since said layer 1 can also deflect mechanical actions on the wound, said depot layer 1 can also be referred to as a cushion or pad. The thickness of the depot layer 1 will be, for example, between 1 mm and 2 mm. The pad 1 extends virtually over the entire surface of the compress. Loosely carded cottonwool forms the material of said depot layer 1. The cottonwool may consist solely of cotton or it may be a mixture of different fibers. Advantageously, the cottonwool comprises 80% cotton or viscose fibers and 20% polyester fibers.

The side of the depot layer 1 which faces the wound side of the compress is provided with a so-called guiding layer 2. Said guiding layer 2 is constructed so that the secretion which passes from a wound to the compress spreads out predominantly along said layer 2, before it reaches the depot layer 1. Hence said layer 2 guides the flow of the secretion in the direction of the surface of the compress. In order to achieve this effect, channels 3 are formed in the surface of the guiding layer 2 which faces the front side of the compress. Said channels 3 extend in the direction of the longitudinal dimension of the guiding layer 2 of the compress. In practice, said channels 3 may be U- or V- shaped in cross-section.

The guiding layer 2 is made of or at least contains fibers which advantageously form a nonwoven material. It may be a mixture which comprises 80% cotton or viscose fibers and 20% polyester fibers. The initially loose fibers form a thick layer which is pressed together (calibrated), to give a relatively thin layer approximately 0.5 mm to 1 mm thick. Channels 3 are formed in said layer 2 by local and permanent compaction of the fibers (stamping) in elongate regions of the guiding layer 2. The thickness of the fibers in the region of the base 4 of the channels 3 is hence greater than the thickness of the fibers in the region of the channel walls 5. The channels 3 open out towards the front side of the compress. The upper opening of the respective channel 3 is limited by the upper borders 6 of the side walls 5 of the channel 3 and for this reason the channel opening is also designated 6 here. The channel opening 6, as can be seen from what has just been described, faces away from the depot layer 1. The underside of the fiber layer forming the channel base 4 is in direct contact with the upper side of the depot layer 1. This allows the secretion to flow from the guiding layer 2 into the depot layer 1.

In the example illustrated in FIG. 1, the channels 3 have a so-called zigzag profile and they are separated from one another by unstamped and hence raised sections 7 of the material of the guiding layer 2. Obviously, said raised guiding layer sections 7 run parallel to the channels 3, which they separate from one another. Only parts of that one of the raised sections 7 shown in FIG. 1 which is at a distance from the rolled up ply 10 are illustrated in triangular outline. These parts were produced because of the section made in FIG. 1.

The channels 3 illustrated in FIG. 1 run essentially parallel to one another and run transverse to the larger longitudinal dimension of the compress. However, it is understood that the channels 3 may also run parallel to the larger longitudinal dimension of the compress. Other forms of channels 3 are also possible. For example, the channels 3 may intersect, they may form specific configurations etc. The depth of the channels 3 is obviously smaller than the thickness of the guiding layer 2. The thickness of the channel base 4 may be equal to the depth of the channel 3 or it may be smaller than the channel depth.

Active substances such as activated carbon, bloodstaunching components or the like may be added to the material of the guiding layer 2. Moreover, it is possible to replace the guiding layer 2 with a layer of a material which forms a gel when it is moistened.

The front side of the guiding layer 2 is provided with a surface ply 10 which covers the openings 6 in the guiding layer 2 and which forms the front seal of the compress. The surface ply 10 is constructed in such a manner that it is permeable for the secretion coming from the wound and does not adhere to the wound. It may be made, for example, from a perforated aluminum foil, if the compress is intended to cover burns. However, the surface ply 10 may also be made of fibers which form at least one layer.

In the illustrated example, the surface ply 10 has two layers 11 and 12 made of fibers, the first layer 11 of which is located on the outer side of the surface ply 10. The second layer 12 is arranged on the side of the surface ply 10 which faces the guiding layer 2. The layers 11 and 12 are intimately joined to one another so that they cannot be separated from one another. Said intimate joining of the layers consisting of fibers may be obtained, for example, by lamination. A mixture of fibers of both types is present in the transitional region of the said layers. Advantageously, the fibers of the surface ply 10 form a nonwoven material.

The liquid is not stored in the surface ply 10 because said ply 10 is very thin, because the material of said ply cannot be wetted by the wound secretion and because the wound secretion may enter unhindered the free space of the channels 3. To be precise, the upper openings 6 of the channels 3 abut the reverse side of the surface ply 10. The capillary forces also help here to suck the wound secretion into the channels 3, because the width of the channels is very small. The channels 3 may be between 0.25 mm and 1 mm wide. Moreover, further individual fibers of the material of the guiding layer 2 project into the cavity of the respective channel 3, which can be well wetted by the secretion. Consequently, the surface of the wound remains relatively dry and the wound may heal rapidly.

The external layer 11, which may also be referred to as the top layer, contains in particular fibers of a material, for example polypropylene, which repels the wound secretion. The thickness of the top layer 11 is selected so that the secretion which possibly may even be viscous, may pass through said layer 11, without a substantial resistance being offered to the passage of the secretion by the top layer 11.

The inner layer or binder layer 12 of the surface ply 10 contains predominantly fibers of a material, for example polyethylene, which enables the fibers of the top layer 11 of the surface ply 10 and the fibers of the guiding layer 2 to be joined. Hence the binder layer 12 serves as a bonding agent between the polypropylene fibers of the top layer and the calibrated (pressed together) cottonwool of the guiding layer 2.

The back of the depot layer 1 is provided with a layer 15 which is substantially liquid-tight, but is capable of breathing and which constitutes the reverse-side sealing layer of the compress. Said layer 15, which may also be referred to as a protective layer, is constructed as a micrononwoven material, for example of polyethylene. It serves, inter alia, to protect linen from heavily bleeding wounds. The micrononwoven material has a relatively rough surface, so that the reverse side of said protective layer can adhere to the section of linen which abuts the compress. This prevents the compress under the piece of linen from slipping.

The present compress is shown schematically and in exploded view in FIG. 2, so that the function of the compress may be illustrated. The secretion, illustrated by droplets 20, penetrates into the wound side of the compress and passes initially through the surface ply 10. In FIG. 2, this is indicated by the first of the droplets 20 illustrated, part of which can no longer be seen. As shown, the secretion passes through the surface ply 10, without wetting it and reaches the guiding layer 2.

The secretion passes through the upper channel opening 6 into the channel 3 and usually fills said channel. Here, the secretion spreads out up to the channel base 4. Since the thickness of the fiber material is relatively large in the region of the channel base 4, the secretion cannot immediately penetrate the channel base 4. Although the thickness of the fiber material in the region of the channel walls 5 is smaller than the thickness thereof in the base region 4, for this reason the path which the secretion must travel is longer when it is to pass from the channel 3 through the channel wall 5 to the depot layer 1. This prevents the secretion, after it has filled the channel 3, from flowing off on this route into the depot layer 1. The resistance which is offered to the flow of the secretion in the channel 3 is substantially lower than the resistance which prevents the secretion from seeping into the channel base 4 and the channel walls 5. Consequently, most of the secretion flows perpendicular to the direction of penetration thereof through the channel 3 to those points of the channel 3 which are not yet filled with the secretion. This is indicated in FIG. 2 with the aid of arrows P1. Since the channels 3 extend in the longitudinal direction of the compress, in this manner the already mentioned fast and effective distribution of the secretion over the surface of the guiding layer 2 and hence also the compress is achieved, before the secretion flows off into the depot layer 1.

The secretion passes from the guiding layer 2 into the depot layer 1 in the region of the point of contact between the underside of the guiding layer base 4 and the upper side of the depot layer 1. This passage is indicated in FIG. 2 with the aid of arrows P2. Said arrows P2 are also intended to indicate that the secretion spreads out from the virtually central point of penetration of the compress right into the corner regions thereof by means of the guiding layer 2. The secretion can pass through the depot layer 1 as far as the sealing layer 15 (arrows P3), where further penetration thereof is, however, prevented, and, to be precise, because of the already described properties of the sealing layer 15.

The depot layer 1 and the guiding layer 2 have virtually the same dimensions. The dimensions of the surface ply 10 and the lower sealing layer 15 are a little larger than the dimensions of the core 1 and 2 of the compress, so that the surface ply 10 and the sealing layer 15 have edges 16 and 17 respectively which project from the core 1, 2. The width of said projecting edge parts 16 and 17 is selected to be only large enough for the edges 16 and 17 to be able to be bonded to one another and for the core 1, 2 not to be able to move in a sheath 10, 15 of this type.

Before the individual plys of the present compress are connected to one another, said plys are prepared separately. The guiding layer 2 is produced by calibration of a cottonwool ply and by stamping of a layer of this type, the channels 3 being produced by the stamping. Where appropriate, the calibration and stamping may be carried out in a single operation.

The surface ply 10 is produced by bringing together the material of the top layer 11 and that of the binder layer 12 and by joining said plys 11 and 12 intimately, for example by lamination. During the production process, the outer side of the top layer 11 is ironed, with the result that the surface of said top layer 11 becomes smooth and shiny, which is one of the reasons why the surface ply 10 does not adhere to the wound.

The material of the surface ply 10 is then heated and placed on the upper side of the guiding layer 2 where said surface ply 10 may cool down. In this process, adhesion occurs between the material of the binder layer 12 and that of the guiding layer 2. The material of the depot layer 1 is then supplied to the side of the guiding layer 2 which faces the back of the compress. The material of the sealing layer 15 is assigned to the back of the depot layer.

Advantageously the materials of the individual plys 1, 2, 10 and 15 form webs which are brought together during the production process and are fed into an apparatus where the individual compresses are cut out from this sandwich. This may be effected, for example by application of ultrasound technology which is known per se.

At the same time as removal of the compress from the web, the edge parts 16 and 17 of the surface ply 10 and the sealing ply 15 are bonded together. The already mentioned rounding of the corners 18 of the compress is also carried out during the cutting out of the compress. The compresses are softly seamed all round and no fiber particles can escape therefrom.

FIG. 3 shows in plan view a section of a further embodiment of the present compress. The individual components of said compress are at least substantially the same as the components of the compress which has been described for example in connection with FIG. 1 here.

The fact that the surface of the pad laid on a wound grows into the skin cells newly formed in the wound, causes considerable problems for the application of compresses or wound pads. When the dressing is changed, the cells fused with the wound pad are pulled off the wound, causing disturbance of the cell formation process and delaying healing of the wound. In order to obviate this disadvantage, a spacer 25 (FIG. 3) is located on the outer side of the surface ply 10 of the compress. The spacer 25 covers at least part of the outer side of the surface ply 10 and it is made of a non-wettable material. Advantageously, this material is a metal, such as silver or gold.

Furthermore, breathing of the skin under the compress must be facilitated as far as possible For this reason, the spacer 25 is constructed as a net-like structure, through the meshes of which both air and liquids, in particular the wound secretion, may pass. Since the spacer 25 has only a single layer and since the surface of said spacer is made of a non-wettable material, the wound secretion is not absorbed by the spacer 25, instead it penetrates therethrough and passes through the surface ply 10 into the body of the compress, where it is received and stored.

The spacer or netting 25 may be made of a metal, such as silver or gold. However, the netting 25 may also be constructed so that the core thereof is made of a plastic, such as polyester, polyamide or polypropylene and so that the surface of said core is coated with a metal. Since gold and silver are relatively expensive materials, the spacer 25 constructed in this manner may be produced more cost effectively than the purely metal spacer. In addition, by virtue of the advantageous properties of plastic for this application, the tensile strength of the only metallized spacer 25 may be even greater than the tensile strength of a metal spacer.

The form and size of the meshes of the net-like spacer 25 are selected such that the wound secretion may pass through the spacer as freely as possible. FIG. 3 shows a netting 25 constructed expediently for the present case, which is applied to the surface layer 10 and firmly connected thereto. In FIG. 3 a section of one of the channels 3 in the guiding layer 2 of the present compress can be seen under the surface layer 10.

The netting 25 has two systems 26 and 27 of strips which are supported on the outer side, that is on the top layer 11 of the surface ply 10. Said strips 26 and 27 are virtually in the same plane and intersect with inclusion of an acute angle between one another. In the region of the points of intersection of said systems of strips 26 and 27 are located two-dimensional accumulations of material 28, with the aid of which the respective point of intersection of two strips 26 and 27 is reinforced. The accumulations of material 28 have a circular contour and the diameter of said accumulations 28 is approximately twice as large as the width of the strips 26 and 27. Because the intersecting strips 26 and 27 are joined in the region of the points of intersection they cannot move in relation to one another.

Furthermore, the netting 25 comprises a system of stabilizing strips 30, which advantageously have the same width as the diagonal strips 26 and 27. The stabilizing strips 30 are in the same plane as the diagonal strips 26 and 27 and the accumulations of material 28. The respective stabilizing strip 30 passes through the points of intersection 28 which lie behind one another in the longitudinal direction thereof. It may also be said that the respective section of the stabilizing strip 30 which extends between two points of intersection 28 is connected in the same manner as the corresponding sections of the diagonal strips 26 and 27 to the accumulations of material 28.

The effect of the presence of the stabilizing strips 30 is that the netting 25 is not stretchable in the direction of the connecting strips 30, whereas the netting is stretchable in the direction perpendicular thereto. If it seems expedient, the netting 25 may also have a second system of stabilizing strips (not shown) which run or stand perpendicular to the stabilizing strips 30 of the first system. A netting of this type is unstretchable in the two directions perpendicular to one another.

FIG. 4 shows in plan view a further embodiment of the present compress. It is known that the passage of electric current, in particular a pulsed current or a low constant current through a point of the wound causes more intensive blood circulation at this point. As a result there is greater metabolism at the point of the wound treated in this manner and hence also this point of the wound receives an improved supply of the body's antibodies.

In order to be able to achieve these effects with the present compress, the outer side of the surface ply 10, that is the top layer 11 of the compress, is provided with electrodes 31 and 32 which adhere to the surface ply 10. In principle two simple electrodes are sufficient to be able to achieve the said effect. However, multiple and/or divided electrodes may also be used for special purposes.

Terminal lugs 33 and 34 are assigned to the electrodes 31 and 32, which terminal lugs are in electrical contact with the electrodes 31 and 32 and to which the wires leading to a source of electric power (not shown) may be connected. In the example illustrated, the terminal lugs 33 and 34 are constructed as U-shaped brackets which are placed on one edge of the compress. The edge part of the textile part of the body of the compress is clamped between the legs of said brackets 33 and 34, so that the brackets 33 and 34 are secured on said part of the body of the compress. The electrode which is assigned to the respective bracket may be clamped between one of the bracket legs and the textile part of the compress. It is understood that the terminal lugs 33 and 34 may also be constructed in another expedient manner and that the electrodes 31 and 32, depending on the manner of construction thereof, may also be connected to the lugs 33 and 34 in another manner.

In the simplest case the electrodes 31 and 32 may be constructed as two strip conductors arranged at a distance from one another, and which are mounted on the outer side of the surface ply 10. If the material of the textile part of the body of the compress, which is located in the gap 35 between two adjacent electrodes 31 and 32, is moistened, for example by the wound secretion, and if electrical voltage is applied to the electrodes 31 and 32, electrical current then flows between the conductor strips 31 and 32. This current flows both through the surface layer 10 and through the wound and said last-mentioned current acts in a healing manner on the wound.

FIG. 4 shows electrodes 31 and 32, each of which has approximately the form of a comb. The distance between the teeth 36 of one of the combs 31 is greater than the width of a tooth 37 of the other comb 32. This allows the teeth 36 of one of the combs 31 to be arranged between the teeth 37 of the other comb 32. In a construction and arrangement of this type of the electrodes 31 and 32, the gap 35 between the electrodes 31 and 32 is very long. Substantially more current can flow transversely through a gap 35 of this length than through a gap between two electrodes 31 and 32 which merely run in a straight line. Moreover, the surface of the wound which can be treated by electrical currents can also be substantially enlarged by arrangement of the electrodes 31 and 32. In practice it may be advantageous for the electrodes to be helicoidal, circular, oval or of some other shape, and to further reorganize the edges of the electrodes by forming smaller teeth etc.

I claim:

1. A compress for dressing wounds, comprising:
   a depot layer for storing secretion from a wound, said depot layer having a first surface and a second surface opposite said first surface, said first and second surfaces being substantially planar;
   a substantially liquid-tight, breathable protective layer applied to said second surface of the depot layer;
   a surface ply having a first surface for application to the wound and a second surface opposite said first surface, said surface ply being permeable to the secretion and non-adherent to the wound; and
   wherein a guiding layer having a first surface and a second surface is between said first surface of the depot layer and said second surface of the surface ply, said guiding layer including a plurality of channels or distributing throughout said guiding layer the secretion which reaches the guiding layer, said channels extending down to a depth from said first surface of the guiding layer;
   wherein said second surface of the surface ply is planar and contacts said fist surface of the guiding layer, whereby said surface ply lies flat over said channels.

2. A compress as recited in claim 1, wherein said channels are substantially parallel to each other.

3. A compress as recited in claim 2, wherein each said channel is defined between said channel walls formed by raised sections of said guiding layer, and above a channel base at said depth below the first surface of the guiding layer.

4. A compress as recited in claim 3, wherein said channels are of zig-zag shape.

5. A compress as recited in claim 3, wherein said guiding layer is a nonwoven material containing fibers, and said channels are formed by compacting said fibers in elongate regions of aid guiding layer whereby said raised sections are formed by the fibers which are non-compacted.

6. A compress as recited in claim 3, wherein said channel base has a thickness less than or equal to the depth of said channel below the first surface of the guiding layer.

7. A compress as recited in claim 3, wherein each said channel has a cross-section which is U-shaped or V-shaped.

8. A compress as recited in claim 3, wherein said guiding layer comprises a nonwoven material containing a mixture of 80% cotton or viscose fibers and 20% polyester fibers.

9. A compress as recited in claim 8, wherein said second surface of the guiding layer contacts said first surface of the depot layer.

10. A compress as recited in claim 8, wherein said guiding layer further comprises activated carbon.

11. A compress as recited in claim 8, wherein said guiding layer further comprises a blood-staunching component.

12. A compress as recited in claim 1, wherein said guiding layer is of a material which gels upon moistening.

13. A compress as recited in claim 1, wherein said depot layer contains loosely carded cottonwool.

14. A compress as recited in claim 1, wherein said depot layer contains a mixture of 80% cotton or viscose fibers and 20% polyester fibers.

15. A compress as recited in claim 1, wherein said protective layer is a micrononwoven material containing polyethylene.

16. A compress as recited in claim 1, wherein said surface ply comprises a repellent layer which repels the secretion and a binder layer between said repellent layer and said guiding layer.

17. A compress as recited in claim 16 wherein said repellent layer contains polypropylene fibers and said binder layer contains polyethylene fibers.

18. A compress as recited in claim 1, wherein said surface ply is a membrane of perforated aluminum foil.

19. A compress as recited in claim 1, further comprising two adjacent electrodes on said first surface of the surface ply.

20. A compress as recited in claim 19, further comprising a terminal lug connected to each said electrode, each said terminal lug comprising a U-shaped bracket located on an edge of the compress.

21. A compress as recited in claim 1, wherein each said electrode is formed as a comb having teeth spaced apart at a distance, wherein the distance between the teeth of each said electrode is greater than the width of each said tooth of the adjacent electrode and the teeth of one said electrode mesh between the teeth of the adjacent electrode.

22. A compress for dressing wounds, comprising:
 a depot layer for storing secretion from a wound, said depot layer having a first surface and a second surface opposite said first surface, said first and second surfaces being substantially planar;
 a surface ply having a first surface for application to the wound and a second surface opposite said first surface, said surface play being a membrane of perforated metal foil;
 a guiding layer between said first surface of the depot layer and said second surface of the surface ply, said guiding layer including guide means for distributing throughout said guiding layer the secretion which reaches the guiding layer; and
 a substantially liquid-tight, breathable protective layer applied to said second surface of the depot layer.

* * * * *